(12) United States Patent
Drew

(10) Patent No.: US 8,383,138 B2
(45) Date of Patent: Feb. 26, 2013

(54) SHARK REPELLING METHOD

(76) Inventor: Anthony Neville Drew, London (GB)

( * ) Notice: Subject to any disclaimer, the term of this patent is extended or adjusted under 35 U.S.C. 154(b) by 1221 days.

(21) Appl. No.: 12/140,998

(22) Filed: Jun. 17, 2008

(65) Prior Publication Data
US 2009/0061012 A1 Mar. 5, 2009

(30) Foreign Application Priority Data
Jun. 24, 2007 (GB) .................... 0712142.9

(51) Int. Cl.
 *A01N 25/00* (2006.01)
 *A01N 25/08* (2006.01)
 *A01N 25/24* (2006.01)
 *A01N 25/26* (2006.01)
 *A01N 25/28* (2006.01)
 *A01N 25/34* (2006.01)
(52) U.S. Cl. ........ 424/405; 424/407; 424/409; 424/411; 424/420
(58) Field of Classification Search .................. None
See application file for complete search history.

(56) References Cited

U.S. PATENT DOCUMENTS

| 3,755,064 A | * | 8/1973 | Maierson | 428/338 |
| 5,069,406 A | * | 12/1991 | Colyer et al. | 248/156 |
| 5,127,860 A | * | 7/1992 | Kraft | 441/74 |
| 5,891,919 A | * | 4/1999 | Blum et al. | 514/625 |
| 2004/0067702 A1 | * | 4/2004 | Thornburg | 441/74 |

* cited by examiner

Primary Examiner — Debbie K Ware

(57) ABSTRACT

A method of repelling sharks for limiting their attacking a surfboard user comprises applying a conventional surfboard traction improving solid wax that also incorporates a shark repellent such as a surfactant, a capsaicinoid or a semiochemical in a concentration based on the "Johnson & Baldridge Test". The extent of application is consequently sufficient to render the coated surfboard foul tasting when bitten by a shark but insufficient to reliably repel a shark in response to the dispersion in the water of the repellent. The invention extends to a shark repellent incorporating surfboard coating wax.

4 Claims, No Drawings

SHARK REPELLING METHOD

FIELD OF THE INVENTION

The present invention claims a priority date of 24 Jun. 2007 from application GB0712142.9 and relates to a method of repelling sharks and to shark repelling waxes used to coat surfboards plus other flotation devices such as wind-surfboards, surf canoes, surf ski's, kayaks, boats, etc.

BACKGROUND TO THE INVENTION

As shark's sense certain irritating substances through free nerve endings (chemoreceptors) located in their mouths which are entirely distinct from their gustatory senses (ie: taste buds) the phrase Oral Repellent (in preference to the more ambiguous term "Gustatory Repellent") is used to describe any substance that irritates either these chemoreceptors and/or the shark's taste buds upon contact with the sharks oral cavity.

Surfers apply Surfboard Wax to the top of their boards to enhance grip between their feet and the board. Different types of surfboard waxes are used for different conditions and water temperatures. Soft, tackier wax is used for cold water and harder base paraffin wax (which melts at a higher temperature) is used for warmer waters. Wax is also applied to body boards and wakeboards for the same reason. Early surfers used candle wax. Then in the 1930s they started using paraffin canning wax. This had to be melted onto the board and created a very hard surface. Sometimes sand would be added into the wax to improve grip. Then, in the 1960s waxes began to be made using oil and soft waxes like beeswax. Later, colors and fragrances were added. Today many of the waxes are synthetic blends of petroleum-based polymers. Some surfers wax the bottom of their boards with wax or fluoropolymer surface coatings to decrease resistance with the water and to protect their board.

In short, surfers have to acquire and replenish a regular supply of one or another embodiment of Surfboard Wax in order to continually coat and re-coat their surfboards and facilitate their sport. It is a cheap, repeat purchase consumable, as essential to the act of surfing as matches/lighters are to the act of smoking.

To this singular end hundreds of brands of Conventional Surfboard Wax are now commercially available, all contriving a distinct profile, but ultimately constituting little more than minor variations on the same industry standard recipe.

Thus the composition of a typical block of Conventional Surfboard Wax defaults to a uniform mixture of circa 60-75% Paraffin Wax, 15-25% Microcrystalline Wax, 5-15% Petroleum Jelly, and 0-10% of a conducive Adhesive plus optional dyes and scents for cosmetic effect.

Note that the above range of percentages enables the manufacturer to tailor the mixture to an optimum consistency and stickiness in a variety of water temperatures. Therefore for warmer water temperatures the amount of microcrystalline wax and adhesive might be increased and the amount of petroleum jelly decreased whereas for colder water temperatures the opposite would hold true.

Note also that different brands substitute different core ingredients to achieve the same objective to a largely identical effect. For example some brands substitute white oil and/or Ceresin Wax for Petroleum Jelly. Others default to an organic recipe of circa 70-80% Beeswax, 20-30% Coconut Oil, and 0-10% Tree Resin. Nevertheless in terms of function and methodology all are effectively indistinguishable.

Meanwhile, shark attack is a long recognized danger faced by ocean going humans and in particular surfers. In fact the definitive statistics collated in tandem by the Florida Museum of Natural History's "International Shark Attack Files" (ISAF) and the Shark Research Committee's "Global Shark Attack Files" (GSAF) both confirm that surfers are now shark's primary targets and are demographically at least 30 times more likely to be attacked than swimmers, divers, fishermen, etc. . . . . .

Historical Development

Of the 300 plus known species of shark (elasmobranches), it is believed that only 35 species have ever attacked humans, and of these barely 15 species are recorded as inflicting repeated attacks. In fact the frequency of worldwide shark attacks on humans is minimal, averaging under 100 unprovoked incidents per year with less than 30% proving fatal.

But despite these statistics, the primordial fear of shark attack has always pre-occupied man and came starkly to the fore during the Second World War when U.S. service personnel were deployed in the shark infested waters of the South Pacific. Thereafter the private and public sector have labored to develop chemical shark repellents potent enough to deter the most aggressive orders of elasmobranches such as carcharhinoformes and lamniformes and afford daily protection and above all peace of mind to the millions of ocean going humans worldwide.

Since then researchers have formulated numerous experiments (bio-assays) to test whether prospective repellents evoke a flight response in sharks. For example, in one such bio-assay a potential repellent of set volume and concentration is introduced into a fixed position in a shark tank and the degree of aversive shark response to that portion of the tank is then recorded.

Another comparable bio-assay introduces a potential repellent of set concentration and volume into the feeding zone of sharks and monitors whether the sharks then flee the vicinity and/or cease feeding activity.

An alternate bio-assay measures the effect of potential repellents on a shark that is trapped in a state of paralysis known as "tonic immobility." Tonic immobility is typically induced when a shark's body is inverted along its longitudinal axis and can persist for up to a quarter of an hour. Researchers then use this 15 minute window to establish behavioral controls and to study the effects of precise concentrations of prospective repellents on the shark. According to this bioessay a successful repellent should waken the shark from its tonic state.

But of all these bio-assays the benchmark was set in 1985 when Johnson & Baldridge and the U.S. Navy established the definitive government target of finding a chemical that would repel sharks when dispersed in a cloud formation in open water at a concentration of 0.1 parts per million (i.e.: 0.1 ug ml-1).

The experiment ("The Johnson & Baldridge Test") stipulated the steady state dispersal of 100 mg of a prospective repellent from a point source into a 6 cubic meter boundary of water over a 3.5 hour period to achieve the proposed 0.1 ppm concentration target in a cloud formation around a potential prey. If sharks then demonstrated strong aversive behavior under these conditions, the criteria was considered satisfied and the repellent was deemed to be "effective".

That goal has yet to be officially achieved. But elasmobranch research history is littered with many near misses and failures.

One of the most notable and earliest of these failures occurred in 1944 with the development of the U.S. Navy's "Shark Chaser" chemical repellent, a mixture of 20% copper acetate and 80% nigrosine dye which was issued to high risk combatants in the Pacific despite being entirely ineffective.

Since then numerous alternative shark repellents methods have been explored with varying degrees of success and practicality including electrical devices (Gilbert & Springer 1963, Gilbert & Gilbert 1973), acoustic devices (Myrberg et al. 1978, Klimley & Myrberg 1979), and visual devices (Doak 1974).

But of the purely chemical methodologies investigated such as toxins and saponins, etc. . . . (Tuve 1963, Clark 1974, Gruber & Zlotkin 1982, Zahuranec & Baldridge 1983) none were considered sufficiently effective (Sisneros (2001)).

A marked advance did occur in 1974 with Eugenie Clark's discovery of the toxin "pardaxin", an amino acid polypeptide secretion of the Moses Sole Fish (Pardachirus marmoratus) which attacked shark's respiratory systems via the gill rakes with significant repellent impact.

However subsequent research revealed that pardaxin and similar natural compounds like pavonin and mosesin were expensive to produce and unstable to store at room temperature. More importantly, it transpired that they were only chemically effective as taste effective (gustatory) repellents rather than smell effective (olfactory) repellents and were thereby deemed functionally impractical to administer at the requisite concentrations as they had to be actively squirted directly into the shark's mouth at the moment of attack as opposed to being passively dispersed in the surrounding water to preemptively target the shark's chemo receptors as per the Johnson & Baldridge test.

A further potential breakthrough was curtailed on identical grounds when Zlotkin noted that pardaxin and its organic affiliates exhibited surfactant properties (i.e.: they reduced surface tension) and speculated that cheap synthetic surfactants such as alkyl sulfates (i.e.: commercial soaps) might also prove viable.

Indeed initial tests by other investigators supported his hypothesis and confirmed that a range alkyl sulfates such as sodium lauryl sulfate (SLS), lithium lauryl sulfate (LLS), sodium octadecyl sulphate (SOS), and sodium dodecyl sulphate (SDS) were all even better than pardaxin at repelling Lemon, Blue, and Great White Sharks and did so with an increasing effectiveness depending on their carbon chain lengths (see "The Behavior and Sensory Biology of Elasmobranch Fishes: An Anthology in Memory of Donald Richard Nelson" (Tricas, T. C. & S. H. Gruber (ed.) (2001)).

But again, subsequent research cited by J. A. Sisneros confounded this breakthrough when he observed that even SDS (the most potent of the alkyl sulfates) was only effective as a repellent at concentration of 43.6 ppm and thus (like pardaxin) still fell short of the Johnson & Baldridge concentration benchmark of 0.1 ppm when dispersed in the surrounding water.

Since then interest has veered back to Semiochemical and even Capsaicinoid based repellents as potential solutions to the Johnson & Baldridge litmus test.

Semiochemicals generically encompass pheromones, allomones, kairomones, attractants, repellants and substances that carry a chemical message and as early as 1978 Hodgeson & Mathewson were describing their irritant effect on lemon sharks. However even then it was recognised that the concentration levels needed to provoke a strong adverse response were pushing the functional limits of the the shark's chemoreceptors. Nevertheless one U.S. based company is currently pursuing two substantiative patents entitled "Elasmobranch-repelling compounds, methods of use (and devices)" which forward prospective solutions based on semiochemicals extracted from shark carcasses (see PCT/US2006/00503 & PCT/US2006/02291 respectively).

Capsaicinoids, meanwhile, are a naturally occurring family of highly pungent compounds responsible for the burning taste produced by all hot peppers. The most potent of these is capsaicin which has been a staple animal deterrent for decades and is the core ingredient in anti-personnel devices such as pepper spray. Capsaicinoid pungency is measured on a gustatory sliding scale of 0-16,000,000 developed by William Scoville in 1912. According to this scale a "Scoville Value" of 1 can barely be tasted, whereas a jalapeno pepper has a value of circa of 2,500-5,000, cayenne pepper has a value of 30,000-50,000 (which is is more than sufficient to taste aversive to a shark) and anything with a value of above 200,000 would cause permanent damage to skin and nerve endings.

Types of Repelling Actions

There are broadly two types of Shark Repellent Device, each with its' own shortcomings with respect to achieving an optimum balance between cost, effectiveness, and convenience:

(1) The first type falls outside the scope of this patent and include the various electrical, mechanical, and sonic repellents. Though arguably effective, these devices are often expensive and/or cumbersome, vulnerable to malfunction, and generally require waterproof electrical batteries with limited energy supplies in order to operate.

(2) The second type includes the various Chemical Repellents, to which this patent pertains. Note that these devices are by nature dual faceted, a fact acknowledged in paragraph 26 of a recent capsicum related shark repellent patent (U.S. Application 179118) which freely concedes that " . . . it is recognized in this invention that a chemical deterrent does not work alone by itself without a device constructed to repel sharks in certain and determined circumstances."

Thus all Shark Repellent Chemical Devices combine a Chemical Agent in an embodiment that simultaneously provides a functional Method of Delivery for that Agent's deployment. In this respect there are broadly four classes of viable Shark Repellent Chemicals:

A) Organic Surfactants—such as pardaxin, pavonin, mosesin and assorted saponins (including phytolacca americana, eremocarpus setigerus, and chlorogalum pomerolk sallet based compounds), etc. . . . .
B) Synthetic Surfactants—such as the alkyl sulfates (including sodium lauryl sulfate, lithium lauryl sulfate, sodium octadecyl sulfate and sodium dodecyl sulfate based compounds), etc. . . . .
C) Capsaicinoid based compounds.
D) Semiochemical based compounds.

Simultaneously there are broadly two established Methods of Delivery for deploying these Chemical Agents:

A) "Continual Dispersion" devices function by continually leaking an ongoing percentage of the Chemical Agent into the surrounding waters in a cloud formation of sufficient concentration to repel any shark intrusion into the immediate vicinity of its human prey. Devices of this type are therefore compromised by the untenably short term, wasteful and expensive nature of their delivery, and above all by their uniform inability to achieve and maintain the 0.1 part per million concentration benchmark dictated by Johnson & Baldridge.
B) Conversely, "One Shot" Devices require that the Chemical Agent be retained in a sealed configuration which is then manually breached by the human target and targeted directly at the shark in response to an imminent attack. While negating the shortcomings of the "Continual Dispersion" method and potentially satisfying the dictates of the Johnson & Baldridge concentration target, this ad hoc approach is itself compromised by its' short term effectiveness and unrealistic reliance on the human target's continual vigilance in the face of a stealthy physically superior predator in an already hostile and uncertain environment.

Problem Analysis

It can therefore be seen that the historic inability of prospective Shark Repelling Devices to achieve their objective by chemical means and in accordance with the Johnson & Baldridge concentration target is rooted in a fundamental paradox.

On the one hand, according to Eugenie Clarke's own Mote Laboratory, they have failed because their efficacy in sea situations is minimal due to the rapid dilution of chemicals in seawater.

On the other hand, all attempts to redress this failure have proved functionally counterproductive. To quote J. A. Sisneros criticism re SLS (and by implication all comparable surfactant based devices), . . . "the greatest limitation of SLS is that it is required to be squirted into the mouth of an approaching shark. It is not effective in surrounding-cloud mode dispersions. Therefore, SLS is only useful when the user can clearly see an approaching shark and orchestrate the delivery of SLS into the animal's mouth."

In other words, thus far all combinations of Chemical Agent and Method of Delivery have proved mutually incompatible. Either a viable (0.1 ppm) concentration of the Chemical Agent has been deployed via an impractical Method of Delivery (as in the squirt approach), or a functional Method of Delivery has been utilized to deploy an insufficient/unsustainable concentration of the Chemical Agent (as in the cloud dispersal approach). But to date no single Device has viably combined both elements.

It is however interesting to note that, irrespective of their differences, all these Devices share two fundamental similarities:

(1) Firstly, they all share a common Design Objective, namely to decrease a potential victim's risk of injury from shark attack in a relatively cost efficient, effective, and convenient manner.

(2) Secondly, they all share a common Design Dynamic, namely the pre-emptive deployment of a shark repelling agent via one of the two aforementioned Methods of Delivery (i.e.: "Continual Dispersion" or "One Shot") in order to deter an attack prior to the shark first biting it's target.

It is an objective of this invention to address the above discussed problems.

SUMMARY OF THE INVENTION

In summary, this invention may be physically realized in any number of non limiting formats, but broadly defaults to the same hand held dimensions, constituents and optional applicability as Conventional Surfboard Wax (as previously described), with the inventive addition of a combination of circa 1%-20% shark deterring Oral Repellent/s (as previously described) and (optional) compensatory Solvents and/or Adhesives in its mixture in forming a shark repellent incorporating wax.

Note that the above Solvents are optionally included to assist transfer of the Oral Repellent upon contact with the shark's oral cavity, and that a non-limiting list of it's potential embodiments is herein taken to include hexane, benzene, dicloroethane, xylene, methylethyl ketone and methyl isobutyl ketone, methylethyl ketone and toluene, dichloromethane and dichloroethane, propylene and acetone, n-propanol, isopropanol, glycol ethers, methanol/ethanol systems, acetic acid, hydrochloric acid solutions, butanol, dimethylsulfoxide, and other short-chain aldehydes and ketones Note also that the above Adhesives are optionally included to achieve the same function as the Solvents and/or offset any loss of viscosity imparted on the original compound by the aforementioned additives, and that a non-limiting list of it's potential embodiments is herein taken to include polyisobutylene and microcrystalline wax.

Note finally that this invention is formed by heating any it's constituent solids (with the provisional exception of any powders) to their respective melting points, then pouring all the constituent ingredients into a uniform mixture which then cools and sets at room temperature to form a solid compound in the form of a shark repellent incorporating wax which can thereafter be employed to coat and recoat the surface of any of a variety of flotation devices to shark deterring effect as previously described.

This invention thus constitutes a tenable, convenient, and cost effective supplement to the existing range of Shark Repellent Devices by innovatively abandoning their pre-emptive Design Dynamic in favor of a unique post hoc Method of Delivery which seeks to deter the shark after rather than before the first bite is taken, thereby providing a modest but tangible reduction in a surfer's (windsurfer's, canoeist's, etc. . . . ) overall risk from shark attack.

To this end, this invention is further innovative in that:
1) It creatively exploits a recently discovered weakness in the shark's habitual attack pattern (i.e.: it's "taste test" proclivity).
2) Unlike all the other Shark Repelling Chemical Devices, it is essentially non-ablative, and forgoes any reliance on the external dispersal/projection of its Chemical Agent in order to achieve its Design Objective.
3) It delivers it's Oral Repellent directly into the shark's mouth without the unrealistic reliance on human vigilance that hampers all the "One Shot" Devices.
4) More importantly, it delivers it's Oral Repellent far more efficiently than any of the "Continuous Dispersal" Devices, thereby surpassing their potency threshold to achieve the Johnson & Baldridge concentration target of 0.1 parts per million at the point of impact with the sharks senses. It attains this crucial potency advantage because:
   i. It retains it's Oral Repellent in an essentially non-ablative wax solid rather than dispersing it as a liquid or powder which would then dilute in the surrounding water.
   ii. Thereafter, it deploys it's Repellent inside the shark's mouth in a fragmented distribution pattern of concentrated wax clusters rather than the uniform distribution pattern typical of other Chemical Devices which inadvertently serve to further dilute the net efficiency of their respective Repellents.
5) Finally, its core recipe can be optionally refined within this scope of this patent by adding further compensatory Adhesives and/or Waxes to impart the compound with the same consistency and utility as Conventional Surfboard Wax, thereby investing it with the binary function of augmenting the traction between surfer and surfboard while simultaneously retaining its primary shark deterring applicability.

The objective of the invention is thus met by firstly providing a physical application which, irrespective of it's dispersant properties in water (or lack thereof), tastes unpleasant/repellent to one or more species of potentially predatory shark when physically ingested and which, given many shark's established propensity to sample their prey before optionally devouring it, thereby tangibly reducing a surfer's (or windsurfer's, kayaker's, canoeist's, etc. . . . ) overall risk of injury from shark attack once it is adhered to the surface of his/her affiliated flotation device (i.e.: surfboard, wind-surfboard, kayak, canoe, etc. . . . ). The invention further tangibly reduces a surfer's (or windsurfer's, kayaker's, canoeist's, etc. . . . ) overall risk of injury from shark attack at minimum cost and with maximum convenience, and thereby provides a tenable commercial supplement/alternative to the existing range of available Shark Repellent Devices. Indeed of the dozens of Methods of Delivery optioned in the aforementioned Semiochemical and Capsaicinoid based patents (including time release sponge-materials attached to surfboards; pump delivery devices affixed to surfboards; pressurized delivery devices affixed to surfboards; and surfboards incorporating hollow chambers from which to disperse repellents) no claim is made to any comparable methodology. The invention also provides a physical application which (given further modification within the scope of this patent) can be utilized like Conventional Surfboard Wax to enhance the traction between surfer and surfboard while simultaneously fulfilling the primary and secondary objectives (as described above).

DETAILED DESCRIPTION OF EMBODIMENTS OF THE INVENTION

It is to be understood that the invention is not limited in its application to the details of construction and to the arrangements of the components set forth in the following description. The invention is capable of other embodiments and of being practiced and carried out in various ways. Also, it is to be understood that the phraseology and terminology employed herein are for the purpose of the description and should not be regarded as limiting.

Example A

To the accomplishment of the above and related objectives, this invention may be embodied in the form of a solid 85 gram block of wax blended from a uniform mixture of Paraffin wax, Beeswax, and a functional concentration of Moses Soul Flat Fish extract (a naturally occurring milky secretion with established shark-deterring properties), wherein supplementary coloration and perfumes can be readily added depending on users' preferences and feeling can be adjusted depending on users requirements and seasonal water temperatures.

Example B

To the accomplishment of the above and related objectives, this invention may also be embodied in the form of a solid 100 gram block of wax blended from a uniform mixture of Paraffin wax, Beeswax, and a functional concentration of Sodium Lauryl Sulfate (a known shark repellent), wherein supplementary coloration and perfumes can be readily added depending on users' preferences and feeling can be adjusted depending on users requirements and seasonal water temperatures.

Example C

To the accomplishment of the above and related objectives, this invention may also be embodied in the form of a solid 90 gram block blended from 20 wt. % of Japanese wax extracted from Japanese wax trees, 50 wt. % of calcium carbonate, plus additives to control hardness, viscosity and a functional concentration of Oleoresin Capsicum (an active ingredient in pepper spray with known shark-deterring properties), wherein supplementary coloration and perfumes can be readily added depending on users' preferences and feeling can be adjusted depending on users requirements and seasonal water temperatures.

Example D

To the accomplishment of the above and related objectives, this invention may also be embodied in the form of a solid 80 gram block blended from a synthetic blend of petroleum-based polymers and a functional concentration of Shark Carcass Semiochemicals (a naturally occurring extract with shark-deterring properties), wherein supplementary coloration and perfumes can be readily added depending on users' preferences and feeling can be adjusted depending on users requirements and seasonal water temperatures.

Example E

To the accomplishment of the above and related objectives, this invention may also be embodied in the form of a solid 100 gram block blended from a mixture of 60% Paraffin Wax, 25% Microcrystalline Wax, 1% Petroleum Jelly, 10% of a conducive Adhesive (as non-limitingly described above), plus 2% of a conducive Organic Surfactant (as non-limitingly described above), plus 2% of a conducive Solvent (as non-limitingly described above), wherein supplementary coloration and perfumes can be readily added depending on users' preferences and feeling can be adjusted depending on users requirements and seasonal water temperatures.

Example F

To the accomplishment of the above and related objectives, this invention may also be embodied in the form of a solid 100 gram block blended from a mixture of 60% Paraffin Wax, 25% Microcrystalline Wax, 1% Petroleum Jelly, 10% of a conducive Adhesive (as non-limitingly described above), plus 2% of a conducive Synthetic Surfactant (as non-limitingly described above), plus 2% of a conducive Solvent (as non-limitingly described above), wherein supplementary coloration and perfumes can be readily added depending on users' preferences and feeling can be adjusted depending on users requirements and seasonal water temperatures.

Example G

To the accomplishment of the above and related objectives, this invention may also be embodied in the form of a solid 100 gram block blended from a mixture of 60% Paraffin Wax, 25% Microcrystalline Wax, 1% Petroleum Jelly, 10% of a conducive Adhesive (as non-limitingly described above), plus 2% of a conducive Capsaicinoid based compound (as non-limitingly described above), plus 2% of a conducive Solvent (as non-limitingly described above), wherein supplementary coloration and perfumes can be readily added depending on users' preferences and feeling can be adjusted depending on users requirements and seasonal water temperatures.

Example H

To the accomplishment of the above and related objectives, this invention may also be embodied in the form of a solid 100 gram block blended from a mixture of 60% Paraffin Wax, 25% Microcrystalline Wax, 1% Petroleum Jelly, 10% of a conducive Adhesive (as non-limitingly described above), plus 2% of a conducive Semiochemical based compound (as non-limitingly described above), plus 2% of a conducive Solvent (as non-limitingly described above), wherein supplementary coloration and perfumes can be readily added depending on users' preferences and feeling can be adjusted depending on users requirements and seasonal water temperatures.

Example I

To the accomplishment of the above and related objectives, this invention may also be embodied in the form of a solid 100 gram block blended from a mixture of 60% Paraffin Wax, 24% Microcrystalline Wax, 1% Petroleum Jelly, 10% of a conducive Adhesive (as non-limitingly described above), plus 5% of Sasol Wax® Product Code: 0801925 (a prototype Capsiacinoid bearing wax compound uniquely researched and manufactured by Sasol Wax Gmbh® to the furtherance of this application), wherein supplementary coloration and perfumes can be readily added depending on users' preferences and feeling can be adjusted depending on users requirements and seasonal water temperatures.

The current invention therefore proposes the non-limiting inclusion of one or more Surfactant/Capsaicinoid/Semiochemical based Oral Repellents into a range of wax based mixtures (akin to Conventional Surfboard Wax) to create an new essentially non ablative repellent incorporating wax ("Beach Wax"). This can then be used to coat any of a range of flotation devices (such as surfboards, kayaks, etc. . . . ) thereby rendering that device foul tasting to a shark by leaving repellent-bearing wax fragments in the shark's mouth when it bites said device, and thus deterring potential secondary attacks on said device (and it's affiliated surfer, canoeists, etc. . . . ) following it's initial ingestion by a shark.

Though at first it might seem counter intuitive and indeed redundant to propose an invention which deters a shark attack after the event, it is precisely the non-pre-emptive methodology of the repellent incorporating wax of the invention that makes it non-obviously innovative.

By way of explanation, recent research conducted pursuant to this patent reveals that:

(A) Sharks tend to misconstrue surfer and surfboard (i.e.: human and affiliated flotation device) as facets of a single undefined prey and have a consistent (circa 50%) predilection to take a small non-lethal "Taste Test" of such prey before deciding whether to return and devour it. This proclivity goes some way to explaining why circa 70% of shark attack victims survive the encounter despite being largely at the shark's mercy. More importantly it is a behavioral characteristic uncommon to most predators and constitutes a non-obvious potential weakness in the shark's established attack pattern which this invention seeks to creatively exploit. To cite a recent National Geographic® article, "There is good and bad news for surfers regarding the great white shark. The bad news, according to shark scientists, and contrary to popular opinion, is that great whites are sharp sighted, curious animals, prone to taking "taste tests" of unfamiliar objects that catch their eye."

(B) A superficial inspection of the "Global Shark Attack Files" (GSAF) suggests that circa 9% of attacks on surfers result in the shark simultaneously and/or exclusively biting into their surfboard. However a more probing investigation into a sample of these case histories conducted by this patent's author (Anthony Drew) suggests that the true figure is at least double this and probably exceeds 20%.

\* For further information see:

The GSAF spreadsheet noting that column J ("Injury") inaccurately implies that only 9 out of the last 100 attacks on surfers dating between September 2003 and January 2007 resulted in a board bite, whereas further analysis of the press archives by Anthony Drew reveals that board bites also occurred in at least another 13 of these cases (see case history's 3380, 3422, 3445, 3464, 3467, 3488, 3506, 3542, 3549, 3555, 3557, 3665, 3667) and that the true figure therefore stands at a minimum of 22.

(C) This therefore implies that in the event of an attack on a surfer there is a conservative (50%×20%=) 10% chance of the shark conducting an initial "taste test" during which it will simultaneously or exclusively bite into the affiliated surfboard. It follows that in these instances the shark will be less inclined to launch a potentially fatal follow-up attack on the surfer if the surface of his/her surfboard has previously been modified to taste unpleasant/repellent to the shark.

(D) Furthermore this statistic can reasonably be assumed to hold true as a minimum percentage for attacks on all comparable flotation devices and to rise in instances of attacks on surf-canoeists/kayakers/etc. . . . where the flotation device in question better insulates the user from direct contact with the water.

The invention claimed is:

1. A method of repelling sharks for limiting their attacks on a human surfboard user comprising the steps of:
   a) providing a solid surfboard wax consisting essentially of an effective concentration of an oral shark repellent suitable for providing traction between the human surfer and a surfboard; and
   b) applying said solid wax of step a) to coat said surfboard in order to achieve the traditional function of providing traction between the human surfer and the surfboard, and also to simultaneously render the surfboard foul tasting to a shark by leaving an effective concentration of said oral shark repellent in the form of solid wax fragments in the mouth of the shark after a first attack on the human surfer, wherein said effective concentration of said oral shark repellent is thereby sufficiently compacted to repel the shark after biting the wax coated surfboard directly but is still insufficient to preemptively repel the shark from the immediate vicinity of the surfboard in response to dispersion and dilution of said oral shark repellent in the surrounding water.

2. A method as claimed in claim 1 wherein said oral shark repellent is a surfactant based compound or solution.

3. A method as claimed in claim 1 wherein said oral shark repellent is a capsaicinoid based compound or solution.

4. A method as claimed in claim 1 wherein said oral shark repellent is a semiochemical based compound or solution.

\* \* \* \* \*